US005804551A

United States Patent [19]
Burhop

[11] Patent Number: 5,804,551
[45] Date of Patent: Sep. 8, 1998

[54] PRETRAUMATIC USE OF HEMOGLOBIN

[75] Inventor: Kenneth E. Burhop, Mundelein, Ill.

[73] Assignee: Baxter International Inc., Deerfield, Ill.

[21] Appl. No.: 747,191

[22] Filed: Nov. 12, 1996

[51] Int. Cl.$^6$ .......................... A61K 37/02; A61K 35/14
[52] U.S. Cl. .............................. 514/6; 530/385; 530/829; 424/529; 424/530
[58] Field of Search ................................ 514/6; 530/385, 530/829; 424/529

[56] References Cited

U.S. PATENT DOCUMENTS

| | | |
|---|---|---|
| 4,911,929 | 3/1990 | Farmer et al. . |
| 4,994,444 | 2/1991 | Zikria . |
| 5,295,944 | 3/1994 | Teicher et al. ................................ 600/1 |
| 5,296,466 | 3/1994 | Kilbourn ..................................... 514/6 |
| 5,334,706 | 8/1994 | Przybelski ............................... 530/385 |
| 5,344,393 | 9/1994 | Roth et al. ................................... 604/4 |
| 5,428,007 | 6/1995 | Fischer et al. .............................. 604/6 |
| 5,432,191 | 7/1995 | Abraham et al. . |
| 5,451,205 | 9/1995 | Roth et al. .................................. 604/6 |
| 5,478,806 | 12/1995 | Nho . |
| 5,498,421 | 3/1996 | Grinstaff et al. . |
| 5,571,801 | 11/1996 | Segall et al. . |

FOREIGN PATENT DOCUMENTS

| | | |
|---|---|---|
| 63-208523 | 8/1988 | Japan . |
| 02531661 | 9/1996 | Japan . |
| 92/20368 | 11/1992 | WIPO . |
| 92/20369 | 11/1992 | WIPO . |
| 9316688 | 9/1993 | WIPO . |
| 95/03068 | 2/1995 | WIPO . |
| 9524213 | 9/1995 | WIPO . |
| 96/29346 | 9/1996 | WIPO . |
| 9640782 | 12/1996 | WIPO . |

OTHER PUBLICATIONS

Zauder Anethesiology Clinics of North America 8(3): 471–479, 1990.
Rabinovici et al. Circulatory Shock 29:115–132, 1989.
Gulati et al. Life Sciences 55(1):827–837, 1994.
Dietz et al. Anesth. Analg 82:390–405, 1996.
Garrioch et al. Crit Care Med 24(1): A39 (Abstract), 1996.
Farmer, Hemoglobin–Based Therapeutics: Trials Show Real Potential, Technical Forum–Therapeutics, (2 pages), Reprinted from the Biotechnology Report 1994/95.
Farmer et al., Preclinical Data and Clinical Trials with Diaspirin Cross–linked Hemoglobin, Artif. Red Cells, pp. 177–185, 1995.
Fukushima et al., Clinical Experience of Hemodilution with Fluosol–DA, Jpn. J. Anesthesiol. (Japan), vol. 30, No. 7, pp. 741–745, 1981.
Giordano et al., An Autologous Blood Program Coordinated by a Regional Blood Center: A 5–Year Experience, Transfusion, vol. 31, No. 6, pp. 509–512, 1991.
Greenwalt et al., Perioperative Red Blood Cell Transfusion, J. Amer. Med. Assoc., vol. 260, No. 18, pp. 2700–2703, 1988.

Messmer et al., Present State of International Hemodilution, Eur. Surg. Res., vol. 18, pp. 254–263, 1986.
Przybelski et al., Clinical Studies with Diaspirin Cross–Linked Hemoglobin Solution (DCLHb): A Review and Update, Art. Cells, Blood Subs., and Immob. Biotech., vol. 24, No. 4, p. 407, 1996 (abstract).
Stehling et al., Acute Normovolemic Hemodilution, Transfusion, vol. 31, No. 9, pp. 857–868, 1991.
Zauder, Preoperative Hemoglobin Requirements, Anesthesiology Clinics of North America, vol. 8, No. 3, pp. 471–480, 1990.
Zietlow, An Overview of DCLHb and Blood Substitutes, 8th European Congress of Intensive Care Medicine, Greece, pp. 813–816, 1995.
Zuck et al., Autologous Transfusion Practice, Vox Sang, vol. 58, pp. 234–253, 1990.
Slanetz et al., "Hemoglobin Blood Substitutes in Extended Preoperative Autologous Blood Donation: An Experimental Study," Surgery, vol. 115, No. 2, pp. 246–254, 1994.
Otterbein et al., "Hemoglobin Provides Protection Against Lethal Endotoxemia in Rats: The Role of Heme Oxygenase–1," Am. J. Respir. Cell Mol. Biol., vol. 13, pp. 595–601, 1995.
Alayash, "Hemoglobin and Tissue Oxidants: Physiological Implications and Protective Strategies,"Artificial Cells, Blood Substitutes, and Immobilization Biotechnology, vol. 24, No. 4, p. 298, (abstract), 1996.
Rhea et al., "Vasopressor Effects of Diaspirin Cross–Linked Hemoglobin (DCLHb) in Critically Ill Patients," Critical Care Medicine, vol. 24, No. 1, p. 3 (abstract), 1996.
Simoni et al., "Immunohistochemical Evaluation of Adhesion Molecules and Von Willebrand Factor Expression in Human Coronary Artery Endothelial Cells Incubated with Different Hemoglobin Solutions," Artificial Cells, Blood Substitutes, and Immobilization Biotechnology, vol. 24, No. 4, p. 428 (abstract), 1996.
Simoni et al., "Modified Hb Solution, with Low Prooxidant Potential and Desired Pharmacological and Anti–Inflammatory Properties, Does Not Activate the Transcription Factor NF–kappa B in Human Vascular Endothelial Cells," Artificial Cells, Blood Substitutes, and Immobilization Biotechnology, vol. 24, No. 4, p. 429, (abstract), 1996.
Vercellotti, "Vascular Responses to Hemoglobin Derived Iron: Potential Dangers and Cytoprotective Adaptions," Artificial Cells, Blood Substitutes, and Immobilization Biotechnolgy, vol. 24, No. 4, p. 451, (abstract), 1996.

*Primary Examiner*—Marian Knode
*Assistant Examiner*—Jay F. Williams
*Attorney, Agent, or Firm*—Senniger, Powers, Leavitt & Roedel

[57] ABSTRACT

A method for improving recovery after surgery or an invasive procedure is provided, including administering a hemoglobin preparation to a patient before surgery or an invasive procedure.

22 Claims, No Drawings

PRETRAUMATIC USE OF HEMOGLOBIN

BACKGROUND OF THE INVENTION

The present invention relates to a method for speeding healing or recovery, or decreasing morbidity and mortality, by administering a hemoglobin preparation to a mammal before undergoing a trauma, such as surgery or an invasive medical procedure.

Hemoglobin, the oxygen-carrying pigment found in erythrocytes, has been employed for a wide variety of therapeutic uses in the medical arts. Hemoglobin is primarily used as a blood substitute for transporting and releasing oxygen. It has also been used to treat hypotension, hemorrhage, shock, ischemia, infection, anemia, edema, thrombosis, stroke, hypoxia, cachexia, cardiac arrest, or other conditions. These conditions are treated after the patient exhibits the condition, or after the patient suffers a wound or injury, or undergoes surgery.

Hemoglobin has also been administered as a pretreatment in patients receiving chemotherapeutic agents or radiation for the treatment of tumors (U.S. Pat. No. 5,428,007; WO 92/20368; WO 92/20369), for prophylaxis or treatment of systemic hypotension or septic shock induced by internal nitric oxide production (U.S. Pat. No. 5,296,466), during the perioperative period or during surgery in a method for maintaining a steady-state hemoglobin concentration in a patient (WO 95/03068), and as part of a perioperative hemodilution procedure used prior to surgery in an autologous blood use method (U.S. Pat. Nos. 5,344,393 and 5,451,205).

A need exists for new therapies to accelerate healing and recovery, and to reduce morbidity and mortality associated with surgical and invasive medical procedures.

SUMMARY OF THE INVENTION

Among the objects of the invention, therefore, may be noted the provision of a hemoglobin preparation for improving recovery after surgery or an invasive medical procedure, and the provision of a method therefor.

The present invention provides a method for improving recovery after surgery or an invasive medical procedure, comprising administering an effective amount of a hemoglobin preparation to a patient about to undergo surgery or an invasive medical procedure.

Further scope of the applicability of the present invention will become apparent from the detailed description provided below. However, it should be understood that the following detailed description and examples, while indicating preferred embodiments of the invention, are given by way of illustration only since various changes and modifications within the spirit and scope of the invention will become apparent to those skilled in the art from this detailed description.

DETAILED DESCRIPTION OF THE INVENTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

The contents of each of the references cited herein are herein incorporated by reference in their entirety.

In the present invention, a hemoglobin preparation is administered to a mammal, such as a human patient, about to undergo a surgical procedure or an invasive medical procedure. The beneficial effects resulting from this treatment, i.e., improved recovery after surgery, include a reduction in the time required for healing and recovery after the surgical procedure, as well as a decrease in the probability of morbidity and/or mortality following the surgical procedure.

While not wishing to be bound to any particular theory of the invention, these effects may, in part, be due to a "pre-conditioning" effect induced by hemoglobin. When a patient suffers a trauma (i.e., a wound or injury) resulting, for example, from surgery, an invasive medical procedure, or an accident, the trauma disturbs the patient's homeostasis. The patient's body biologically reacts to the trauma to restore homeostasis. This reaction is referred to herein as a naturally occurring stress response. If the body's stress response is inadequate or if it occurs well after the trauma is suffered, the patient is more prone to develop disorders. When a hemoglobin preparation is administered to a patient before the patient suffers the trauma, the hemoglobin triggers the naturally occurring stress response within the patient's body, thereby preparing the body for the physiological stresses accompanying a trauma. The stress response is initiated before the trauma occurs so that the body is prepared to respond to the physiological stresses when they occur. The pretreatment eliminates the body's delay in triggering the stress response, thereby accelerating healing and recovery, and reducing morbidity and mortality after trauma.

As used herein, the term "surgery" refers to the treatment of diseases, injuries, and deformities by manual or operative methods. Common surgical procedures include, but are not limited to, abdominal, aural, bench, cardiac, cineplastic, conservative, cosmetic, cytoreductive, dental, dentofacial, general, major, minor, Moh's, open heart, organ transplantation, orthopedic, plastic, psychiatric, radical, reconstructive, sonic, stereotactic, structural, thoracic, and veterinary surgery. The method of the present invention is suitable for patients that are to undergo any type of surgery dealing with any portion of the body, including but not limited to those described above, as well as any type of any general, major, minor, or minimal invasive surgery.

Minimal invasive surgery involves puncture or incision of the skin, or insertion of an instrument or foreign material into the body. Non-limiting examples of minimal invasive surgery include arterial or venous catheterization, transurethral resection, endoscopy (e.g., laparoscopy, bronchoscopy, uroscopy, pharyngoscopy, cystoscopy, hysteroscopy, gastroscopy, coloscopy, colposcopy, celioscopy, sigmoidoscopy, and orthoscopy), and angioplasty (e.g., balloon angioplasty, laser angioplasty, and percutaneous transluminal angioplasty).

The method of the present invention is suitable for patients that are to undergo any type of invasive medical procedure, which often cause trauma in patients. Invasive medical procedures include, but are not limited to, general catheterization (i.e., insertion of a catheter into any cavity of the body to withdraw or introduce a fluid), and intubation (i.e., insertion of a tube into a body canal or hollow organ). Intubation includes, for example, endotracheal, nasal, nasotracheal, oral, and orotracheal intubation.

Useful doses of hemoglobin in the present method are those that reduce the time required for healing or recovery after surgery, an invasive medical procedure, or trauma, or which decrease the probability of morbidity or mortality following surgery or trauma.

These results can be achieved with hemoglobin doses in the range of from about 10 mg/kg body weight to about 5,500 mg/kg body weight, more preferably from about 25 mg/kg body weight to about 1,000 mg/kg body weight, and most preferably from about 50 mg/kg body weight to about 400 mg/kg body weight.

Administration of such effective amount of hemoglobin can be carried out parenterally, for example by intravenous or intraarterial injection, infusion, or arterial cannulization (in appropriate clinical circumstances), preoperatively or before a patient undergoes an invasive medical procedure or other trauma. Such effective amount can be administered in a single dose, or in a series of multiple subdoses. The single dose or each of the multiple subdoses can be administered by slow continuous infusion.

Administration of hemoglobin to reduce the time required for healing or recovery after surgery, an invasive medical procedure or other trauma, or to decrease the probability of morbidity and/or mortality following such surgery or trauma, can be via such single dose, or multiple subdoses, given within about 72 hours to about 12 hours prior to the surgery or trauma, more preferably within about 48 hours to about 18 hours, most preferably within about 36 hours to about 24 hours prior to the surgery or trauma.

As used herein, the term "hemoglobin" includes all oxygen-carrying proteins containing globin or globin-like polypeptides and heme, and being capable of transporting and releasing oxygen to cells, tissues or organs when introduced into the blood stream of a mammal in a physiologically compatible carrier. The term "hemoglobin" includes all naturally- and non-naturally-occurring hemoglobin. The term "hemoglobin preparation" includes hemoglobin in a physiologically compatible carrier or lyophilized hemoglobin reconstituted with a physiologically compatible carrier, but does not include whole blood, red blood cells or packed red blood cells.

Naturally-occurring hemoglobin includes any hemoglobin identical to hemoglobin naturally existing within a cell. Naturally-occurring hemoglobin is predominantly wild-type hemoglobin, but also includes naturally-occurring mutant hemoglobin. Wild-type hemoglobin is hemoglobin most commonly found within natural cells. Wild-type human hemoglobin includes hemoglobin A, the normal adult human hemoglobin having two $\alpha$- and two $\beta$-globin chains. Mutant hemoglobin has an amino-acid sequence that differs from the amino-acid sequence of wild-type hemoglobin as a result of a mutation, such as a substitution, addition or deletion of at least one amino acid. Adult human mutant hemoglobin has an amino-acid sequence that differs from the amino-acid sequence of hemoglobin A. Naturally-occurring mutant hemoglobin has an amino-acid sequence that has not been modified by humans. The naturally-occurring hemoglobin of the present invention is not limited by the methods by which it is produced. Such methods typically include, for example, erythrocytolysis and purification, recombinant production, and protein synthesis.

Non-naturally-occurring hemoglobin includes mutant hemoglobin having an amino-acid sequence different from the amino-acid sequence of hemoglobin naturally existing within a cell, and chemically-modified hemoglobin. Such non-naturally-occurring mutant hemoglobin is not limited by its method of preparation, but is typically produced using one or more of several techniques known in the art, including, for example, recombinant DNA technology, transgenic DNA technology, protein synthesis, and other mutation-inducing methods.

Chemically-modified hemoglobin is a natural or non-natural hemoglobin molecule which is bonded to or encapsulated by another chemical moiety. For example, a hemoglobin molecule can be bonded to pyridoxal-5'-phosphate, or other oxygen-affinity-modifying moiety to change the oxygen-binding characteristics of the hemoglobin molecule, to crosslinking agents to form crosslinked or polymerized hemoglobin, or to conjugating agents to form conjugated hemoglobin. Conjugated, polymerized and crosslinked hemoglobins generally exhibit longer intravascular retention times than unmodified hemoglobin.

Several examples of hemoglobin modification technology which can be used in the practice of the present invention have been described in the scientific literature (reviewed by R. M. Winslow (1992) in *Hemoglobin-Based Red Cell Substitutes*, The Johns Hopkins University Press, Baltimore, Md.). Some representative methods of preparing chemically-modified hemoglobin for use in the invention are described below.

Hemoglobin can be modified to improve its oxygen-binding affinity. Reagents that bind to the 2,3-diphosphoglycerate binding site of a hemoglobin molecule, reduce the oxygen affinity of the hemoglobin molecule, and prolong intravascular retention are described in U.S. Pat. Nos. 4,529,719 and 5,380,824 (pyridoxal-5'-phosphate), U.S. Pat. No. 4,600,531 (carboxyl-, phosphonate-, phosphate-, sulfonate- or sulfate-phenyl ester-containing compounds such as mono(3,5-dibromosalicyl)fumarate), U.S. Pat. No. 5,268,500 (arylureido acid compound), U.S. Pat. No. 5,382,680 (2[4-(((benzyl)amino)carbonyl) phenoxy]-2-methyl propionic acids), and U.S. Pat. Nos. 5,290,803 and 5,432,191. In general, any method of preparing or modifying hemoglobin such that the hemoglobin can transport and release oxygen is suitable in the present method. Preferably, the hemoglobin has a $P_{50}$ of between about 20 and about 45 mm Hg.

An encapsulated hemoglobin is hemoglobin surrounded by a material which retains the hemoglobin within the material yet allows smaller molecules to pass through the material to react with hemoglobin and reaction products to pass out of the material. Materials for encapsulating hemoglobin are described in U.S. Pat. No. 4,343,715 (polyurethane, acrylic gels, maleic anhydride polymers, epoxy polymers, glutaronic aldehyde polymers), U.S. Pat. Nos. 5,061,688, 5,217,648 and 5,438,041 (oil emulsion), and U.S. Pat. Nos. 4,322,311, 4,324,683 and 4,390,521 (polymers).

A conjugated hemoglobin is at least one non-hemoglobin molecule covalently or ionically bound to a hemoglobin. In some embodiments, the non-hemoglobin molecule can also form an intermolecular crosslink between hemoglobin molecules. Conjugating materials and methods for preparing hemoglobin conjugates are described in WO 91/07190 (polyalkylene glycol), U.S. Pat. Nos. 4,670,417, 5,091,176, 5,219,564, 5,234,903, 5,312,808 and 5,386,014, WO 94/04193, WO 94/09027 and Japanese Patent Nos. 59-104323 and 61-053223 (polyalkylene oxide), U.S. Pat. Nos. 5,349,001 and 5,405,877 (cyclic imide thione activated polyalkylene oxide), U.S. Pat. No. 4,301,144 (polyalkylene glycol, alkylene glycol copolymers, alcohol-polyalkylene glycol ether copolymers, carboxylic acid-polyalkylene glycol ester copolymers, and amine-polyalkylene glycol derivatives), U.S. Pat. Nos. 4,267,234, 4,267,435 and 4,369,226 (polyglutaraldehyde), Canadian Patent Application No. 2,074,852 (divinyl sulfone), U.S. Pat. No. 4,412,989 (polyether), U.S. Pat. No. 4,377,512 (inulin), U.S. Pat. Nos. 5,079,337 and 5,110,909 (polysaccharide, polyvinyl alcohol, polyvinyl pyrrolidone, polymethacrylate, polypeptide, polyalkylene glycol, hydroxyalkyl starch, and dextran), U.S. Pat. No. 4,920,194 (sulfated glycosaminoglycan fragments, such as heparin), U.S. Pat. No. 4,970,156 (active protein), U.S. Pat. No. 4,336,248 (dialdehyde), U.S. Pat. No. 4,900,780 (hydroxyethyl starch or tetronic polymer), and U.S. Pat. Nos. 4,698,387, 4,935,465, and 5,514,780.

Crosslinked hemoglobin is intramolecularly linked between globin or globin-like protein subunits by a crosslinking agent. A subunit is one globin or globin-like protein of a hemoglobin molecule. Intramolecular crosslinking prevents dissociation of globin or globin-like proteins when hemoglobin is administered in vivo. Hemoglobin A, for example, can dissociate into two α-β globin dimers if the dimers are not crosslinked. Crosslinked hemoglobins and methods for their preparation are described in U.S. Pat. Nos. 4,529,719 and 4,600,531 (α-α linkage using diphenyl ester derivatives such as bis(3,5-dibromosalicyl)fumarate), U.S. Pat. Nos. 4,001,401 and 4,053,590 (α-β globin linkage using halogenated cycloalkanes, diepoxides, and diazobenzidines), U.S. Pat. No. 4,857,636 (aldehyde derived from oligosaccharide), U.S. Pat. No. 5,334,705 (benzenetricarboxylate), WO 94/21682 (P-0 globin linkage using di- or trisaccharide), U.S. Pat. No. 5,290,919 and 5,387,672 (di- or trivalent compounds), U.S. Pat. No. 5,334,707 (β-β or α-α linkage using acyl phosphate ester), U.S. Pat. No. 5,362,885 and WO 92/09630 (imidoesters, such as dimethyl adipimidate or dimethyl suberimidate), U.S. Pat. No. 5,514,780 (polycarboxylic acid), U.S. Pat. No. 5,399,671 and WO 90/13309 (β-β linkage), and U.S. Pat. No. 4,473,496 (dialdehyde).

A polymerized hemoglobin is intermolecularly linked between hemoglobin molecules. Polymerization generally increases the molecular weight of the hemoglobin, which improves its intravascular half-life. Polymerization agents for preparing polymerized hemoglobin are described in pending U.S. applications Ser. Nos. 08/149,679, 08/173,882, 08/480,593, and 08/473,459, U.S. Pat. No. 4,777,244 (aliphatic dialdehyde), U.S. Pat. No. 5,349,054 (benzenepentacarboxylate), WO 94/14460 (transglutaminase), and EP 201618 (glutaraldehyde).

Hemoglobins can also be modified by a combination of the methods described above, for example, as described in Japanese Patent Nos. 59-089629, 59-103322, and 59-104323 (pyridoxal-5'-phosphate modification and polyethylene glycol conjugation of hemoglobin), U.S. Pat. No. 5,248,766 (crosslinking and polymerization of tetrameric hemoglobins with oxiranes), U.S. Pat. Nos. 4,650,786, 4,710,488 and 4,900,816 (inositol phosphate aldehyde modification and polysaccharide conjugation of hemoglobin), U.S. Pat. Nos. 5,189,146 and 5,364,932 (di- or polyaldehydes for intra- and intermolecular crosslinking), EP 361719 (pyridoxylation, dicarboxylic acid halo-ester crosslinking, and polymerization), WO 90/13309 (pyridoxal-5-phosphate derivative for intramolecular crosslinking and glutaraldehyde for polymerization), U.S. Pat. No. 5,439,882 (periodate-oxidized ATP intramolecular crosslinking and periodate-oxidized adenosine polymerization), U.S. Pat. Nos. 4,826,811 and 5,194,590 (pyridoxylation and glutaraldehyde polymerization), and U.S. Pat. No. 4,529,719 (intramolecularly crosslinked with diaspirin ester and pyridoxylated).

Recombinantly-produced hemoglobin is produced by recombinant DNA methodologies, for example, by site-directed mutagenesis, gene fusion, or transfecting a genetically engineered plasmid into a microorganism such as a bacterium or yeast, a cultured cell such as an insect cell, a mammalian cell, or plant cell, a transgenic plant, a transgenic animal, or any other host cell or organism, where the plasmid includes a nucleic acid polymer (e.g., cDNA) which encodes a globin protein, a fusion protein, or a protein similar to globin that can reversibly bind oxygen. Recombinant mutant and artificial hemoglobins and their production in cell cultures or fluids is described in U.S. Pat. Nos. 5,449,759 and 5,028,588, and in WO 88/09179, AU 614525, GB 2234749 B, and EP 358708 BD. Di-α and di-β globin-like polypeptides and other hemoglobin variants produced in bacteria and yeast, and other fused hemoglobins, are described in WO 90/13645, WO 91/16349, EP 561245 A1, and AU 614525. Non-natural multimeric hemoglobin-like proteins are described in WO 93/09143. Production and recovery of human hemoglobin from transgenic pigs are described in WO 92/22646, WO 93/25071, and WO 95/04744. Methods for the preparation and purification of hemoglobin derived from erythrocyte and non-erythrocyte cells are described in WO 92/22646, WO 93/25071, WO 95/04744, WO 95/14038, and WO 96/15151.

Hemoglobins useful in the methods of the present invention are also free of pyrogens, toxins and other contaminants. Pyrogen-free hemoglobin is hemoglobin that is absolutely free of fever-producing contaminants, or hemoglobin that contains amounts of fever-producing contaminants that are physiologically acceptable to a patient to which the hemoglobin will be administered. Bacterial endotoxins contaminate hemoglobin derived from erythrocytes. The endotoxins are released when erythrocytes are disrupted to obtain hemoglobin. Recombinant hemoglobin produced in non-erythrocyte host cells such as bacteria can also become contaminated with cellular components such as proteins, toxins, or polysaccharides that can elicit toxic or pyrogenic responses when administered to mammals (Rietschel et al. (1992) *Scientific American* 267:54–61; Suffredini et al. (1989) *New Eng. J. Med.* 321:280–287).

Hemoglobins for use in the present invention are also stroma-free. Stroma, the insoluble cell membrane fragments that contaminate hemoglobin derived from lysed erythrocytes, is toxic and has been reported to cause dyspnea, bronchospasm, hypotension, arrhythmia, disseminated intravascular coagulation, activation of complement, and renal, myocardial, and hepatic changes associated with ischemia and acute inflammation (Feola (1988) *Surgery, Gynecology & Obstetrics* 166:211–222; MacDonald et al. (1988) *F.A.S.E.B. J.* 2(6) Abstr. 8217;

Stone et al. (1979) *Surgery, Gynecology & Obstetrics* 149:874–876; Rabiner et al. (1967) *J. Exp. Med.* 126:1127–1142. For purposes of the present invention, "stroma-free hemoglobin" is hemoglobin, as defined herein, which is either absolutely free of stroma, or which contains stroma at concentrations that are physiologically acceptable (i.e., do not cause adverse side effects) in a patient. Stroma-free hemoglobin that is absolutely free of stroma includes recombinant hemoglobin produced in a non-erythrocyte. Stroma-free hemoglobin that contains stroma at physiologically acceptable levels includes, for example, purified hemoglobin derived from erythrocytes.

The hemoglobin can be dialyzed or exchanged by ultrafiltration into a physiologically acceptable solution preferably to between about 1 and about 20 g/dl hemoglobin. The solution generally comprises a physiologically compatible electrolyte vehicle isosmotic with whole blood and which maintains the reversible oxygen-carrying and delivery properties of the hemoglobin. The physiologically acceptable solution can be, for example, physiological saline, a salineglucose mixture, Ringer's solution, lactated Ringer's solution, Locke-Ringer's solution, Krebs-Ringer's solution, Hartmann's balanced saline, heparinized sodium citrate-citric acid-dextrose solution, and polymeric plasma substitutes, such as polyethylene oxide, polyvinyl pyrrolidone, polyvinyl alcohol and ethylene oxide-propylene glycol condensates. Such solutions can be administered parenterally, for example by intravenous or intraarterial injection or infusion, without adverse side effects. The hemoglobin can also be lyophilized for storage and reconstituted prior to use. Methods for preparing such solutions or lyophilized powders are known in the art.

A preferred hemoglobin for use in the present method is hemoglobin crosslinked with bis(3,5-dibromosalicyl)-fumarate to create a fumarate crosslink between the two α subunits (DCLHb™, manufactured by Baxter Healthcare, Deerfield, Ill.). This crosslinked hemoglobin is more fully described, together with methods for its preparation, in U.S. Pat. Nos. 4,598,064, 4,600,531, and RE 34,271, omitting the chromatography step. This hemoglobin is preferably manufactured under the conditions disclosed in U.S. Pat. Nos. 4,831,012, 4,861,867, 5,128,452 and 5,281,579 and U.S. patent application Ser. No. 07/207,346.

In practice, a preferred DCLHb™ solution, manufactured by Baxter Healthcare Corporation and useful in the present invention, contains 10 g/dl of modified tetrameric hemoglobin in a balanced electrolyte solution. The product is prepared from units of human red cells from volunteer donors which have been tested and found negative for HbsAg, HIV-1 and 2, and HCV. During manufacture, the red cells are osmotically lysed to release hemoglobin. After ultrafiltration, the stroma-free hemoglobin is reacted with the diaspirin crosslinking agent to produce a stabilized tetrameric hemoglobin having a fumaryl moiety linking the two α subunits. After crosslinking, the reaction mixture is heated to effect viral deactivation and precipitate extraneous proteins. The precipitate is removed by filtration. The DCLHb™ is then concentrated and diafiltered into a physiologic electrolyte vehicle. The resulting solution is isosmotic with whole blood, hyperoncotic (approximately 40 torr), and has the composition shown in Table 1.

TABLE 1

Chemical Assay of 10% Diaspirin Crosslinked Hemoglobin Solution

| | |
|---|---|
| Hemoglobin content | 10 g/dl |
| Oncotic pressure | 43 mm Hg |
| Osmolarity | 290 mOsm/L |
| pH | 7.4 @ 37° C. |
| $Na^+$ | 145 mEq/L |
| $K^+$ | 4 mEq/L |
| $Ca^{++}$ | 2.3 mEq/L |
| $Mg^{++}$ | 0.9 mEq/L |
| $Cl^-$ | 115 mEq/L |
| Lactate | 34 mEq/L |

The invention being thus described, it will be obvious that the same can be varied in many ways. Such variations are not to be regarded as a departure from the spirit and scope of the present invention, and all such modifications and equivalents as would be obvious to one skilled in the art are intended to be included within the scope of the following claims.

What is claimed is:

1. A method for treating a patient before surgery or an invasive medical procedure, comprising scheduling a patient for surgery or an invasive medical procedure, and administering a hemoglobin preparation to the patient before the surgery or the procedure, the surgery or procedure being scheduled after taking into account that the surgery or procedure should be performed more than about 12 hours after initiating the administration, wherein the hemoglobin preparation contains from about 10 milligrams stroma-free hemoglobin per kilogram body weight to about 1,000 milligrams stroma-free hemoglobin per kilogram body weight and the stroma-free- hemoglobin is selected from the group consisting of crosslinked hemoglobin, conjugated hemoglobin, encapsulated hemoglobin and polymerized hemoglobin.

2. The method of claim 1 wherein said invasive medical procedure is catheterization or intubation.

3. The method of claim 1 wherein said mammal is a human.

4. The method of claim 1 wherein said crosslinked hemoglobin is diaspirin-crosslinked hemoglobin.

5. The method of claim 1 wherein the hemoglobin preparation contains from about 25 milligrams stroma-free hemoglobin per kilogram body weight to about 1,000 milligrams stroma-free hemoglobin per kilogram body weight.

6. The method of claim 1 wherein the hemoglobin preparation contains from about 50 milligrams stroma-free hemoglobin per kilogram body weight to about 400 milligrams stroma-free hemoglobin per kilogram body weight.

7. The method of claim 1 wherein said administering is carried out in a time period in the range of from about 72 hours to about 12 hours prior to said surgery or said procedure.

8. The method of claim 1 wherein said administering is carried out in a time period in the range of from about 48 hours to about 18 hours prior to said surgery or said procedure.

9. The method of claim 1 wherein said administering is carried out in a time period in the range of from about 36 hours to about 24 hours prior to said surgery or said procedure.

10. The method of claim 1 wherein said hemoglobin preparation is in the form of a physiologically acceptable solution for parenteral administration.

11. The method of claim 10 wherein said physiologically acceptable solution contains from about 1 g/dl to about 20 g/dl hemoglobin.

12. A method for treating a patient before surgery or an invasive medical procedure, comprising administering a hemoglobin preparation containing from about 50 milligrams stroma-free hemoglobin per kilogram body weight to about 400 milligrams stroma-free hemoglobin per kilogram body weight to a patient within a time period of between about 72 hours and about 12 hours before the surgery or the procedure, wherein the stroma-free hemoglobin is selected from the group consisting of crosslinked hemoglobin, conjugated hemoglobin, encapsulated hemoglobin, and polymerized hemoglobin.

13. The method of claim 12 wherein said administering is carried out in a time period in the range of from about 48 hours to about 18 hours prior to said surgery or said procedure.

14. The method of claim 12 wherein said administering is carried out in a time period in the range of from about 36 hours to about 24 hours prior to said surgery or said procedure.

15. A method for treating a patient before surgery or an invasive medical procedure, comprising administering a hemoglobin preparation containing from about 10 milligrams stroma-free hemoglobin per kilogram body weight to about 1,000 milligrams stroma-free hemoglobin per kilogram body weight to a patient within a time period of between about 72 hours and about 12 hours before the surgery or the procedure, wherein the patient has not received any other dose of a hemoglobin preparation greater than or equal to said concentration during said time period, and the stroma-free hemoglobin is selected from the group consisting of crosslinked hemoglobin, conjugated hemoglobin, encapsulated hemoglobin, and polymerized hemoglobin.

16. The method of claim 15 wherein said crosslinked hemoglobin is diaspirin-crosslinked hemoglobin.

17. The method of claim 15 wherein the hemoglobin preparation contains from about 25 milligrams stroma-free hemoglobin per kilogram body weight to about 1,000 milligrams stroma-free hemoglobin per kilogram body weight.

18. The method of claim 15 wherein the hemoglobin preparation contains from about 50 milligrams stroma-free hemoglobin per kilogram body weight to about 400 milligrams stroma-free hemoglobin per kilogram body weight.

19. The method of claim 15 wherein said administering is carried out in a time period in the range of from about 48 hours to about 18 hours prior to said surgery or said procedure.

20. The method of claim 15 wherein said administering is carried out in a time period in the range of from about 36 hours to about 24 hours prior to said surgery or said procedure.

21. The method of claim 1 wherein the hemoglobin preparation contains from about 50 milligrams stroma-free hemoglobin per kilogram body weight to about 1,000 milligrams stroma-free hemoglobin per kilogram body weight.

22. The method of claim 15 wherein the hemoglobin preparation contains from about 50 milligrams stroma-free hemoglobin per kilogram body weight to about 1,000 milligrams stroma-free hemoglobin per kilogram body weight.

* * * * *

UNITED STATES PATENT AND TRADEMARK OFFICE
CERTIFICATE OF CORRECTION

PATENT NO. : 5,804,551
DATED : September 8, 1998
INVENTOR(S) : Kenneth E. Burhop Page 1 of 1

It is certified that error appears in the above-identified patent and that said Letters Patent is hereby corrected as shown below:

Column 8, Claim 1,
Line 11, "hemoglobin, and" should read ---hemoglobin, recombinantly produced hemoglobin, and---.

Column 8, Claim 12,
Line 54, "hemoglobin, and" should read ---hemoglobin, recombinantly produced hemoglobin, and---.

Column 9, Claim 15,
Line 6, "said concentration" should read ---said preparation---.
Line 9, "hemoglobin, and" should read ---hemoglobin, recombinantly produced hemoglobin, and---.

Signed and Sealed this

Seventeenth Day of July, 2001

*Attest:*

Nicholas P. Godici

NICHOLAS P. GODICI
*Attesting Officer*   *Acting Director of the United States Patent and Trademark Office*